United States Patent
Leysieffer

[11] Patent Number: 5,833,626
[45] Date of Patent: Nov. 10, 1998

[54] DEVICE FOR ELECTROMECHANICAL STIMULATION AND TESTING OF HEARING

[75] Inventor: Hans Leysieffer, Taufkirchen, Germany

[73] Assignee: Implex GmbH Spezialhörgeräte, Ismaning, Germany

[21] Appl. No.: 726,486

[22] Filed: Oct. 7, 1996

[30] Foreign Application Priority Data

May 10, 1996 [DE] Germany .................. 196 18 961.6

[51] Int. Cl.⁶ .................................................. A67B 5/12
[52] U.S. Cl. ........................ 600/559; 73/585; 381/68; 181/126
[58] Field of Search ................... 381/68, 68.1, 68.2, 381/68.3, 68.4, 68.5, 68.6, 68.7, 69; 607/55, 56, 57; 600/25, 559; 623/10; 73/585; 128/746; 181/126

[56] References Cited

U.S. PATENT DOCUMENTS

| | | | |
|---|---|---|---|
| 2,164,121 | 6/1939 | Pescador | 600/25 |
| 3,882,285 | 5/1975 | Nunley et al. | 600/25 |
| 4,850,962 | 7/1989 | Schaefer | 600/25 |
| 5,259,032 | 11/1993 | Perkins et al. | 381/68 |
| 5,277,694 | 1/1994 | Leysieffer et al. | 600/25 |
| 5,318,502 | 6/1994 | Gilman | 600/25 |
| 5,411,467 | 5/1995 | Hortmann et al. | 600/25 |
| 5,430,801 | 7/1995 | Hill | 381/69 |

FOREIGN PATENT DOCUMENTS

| | | | |
|---|---|---|---|
| 0 263 254 | 4/1988 | European Pat. Off. | A61F 11/04 |
| 337590 | 6/1921 | Germany . | |
| 31 21 429 | 2/1983 | Germany | A61B 10/00 |
| 1 354 125 | 5/1974 | United Kingdom | B06B 3/00 |

OTHER PUBLICATIONS

"Klinische Erfahrungen mit der Schallsonde nach Zöllner", Medizinal Marki, Nr. 12, 1956, pp. 444–445.

*Primary Examiner*—Hezron E. Williams
*Assistant Examiner*—Richard A. Moller
*Attorney, Agent, or Firm*—Sixbey, Friedman, Leedom & Ferguson; David S. Safran

[57] ABSTRACT

A device for electromechanical stimulation and testing of hearing in which an electromechanical transducer transmits audiologic signals as mechanical deflections via a coupling element from the outside, noninvasively through the external auditory canal, by direct mechanical coupling with the manubrium of the malleus to the ossicular chain. In preferred embodiments, by suitable selection of the transducer principle disruptive magnetic stray fields and acoustic stimulation by sound transmission to the contralateral ear, which is not being examined, are prevented.

17 Claims, 1 Drawing Sheet

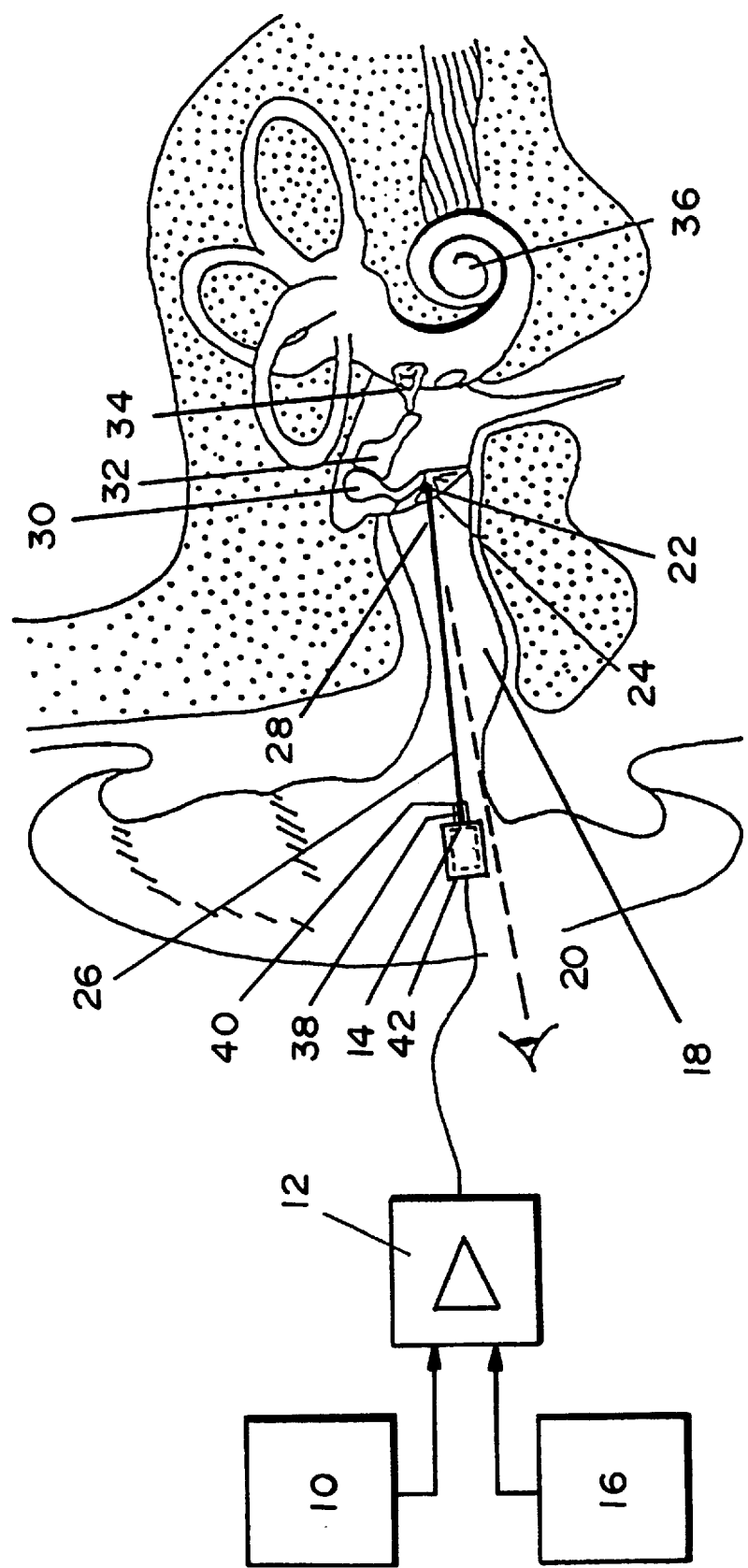

DEVICE FOR ELECTROMECHANICAL STIMULATION AND TESTING OF HEARING

BACKGROUND OF THE INVENTION

1. Field of the Invention

This invention relates to devices for electromechanical stimulation and testing of hearing.

2. Description of Related Art

Generally, the hearing of an individual is tested such that an acoustic signal and, thus, an acoustic wave are presented via suitable electroacoustic means to the subject monaurally (one ear) or binaurally (two ears) and the subject reacts subjectively to corresponding questions which are matched to the respective purpose of the psychoacoustic examination. These electroacoustic means are collectively called audiometers. In the most frequent applications, the test signal is produced either electronically (analog or digital signal generators) or taken from a suitable audio medium (magnetic tape, compact disk, etc.). These test signals are presented to the subject acoustically usually via loudspeakers under so-called free field conditions or via specially calibrated measurement headphones.

In special cases, these acoustic signals are routed via short acoustic conduction hoses and ear adapters to the external auditory canal, when, for example, a volume which is acoustically tightly closed is required in front of the eardrum for special testing. Moreover, there are objective hearing testing methods (for example: BERA: brainstem evoked response audiometry) in which acoustically evoked neuronal responses are picked up via skin electrodes and analyzed accordingly (Boehme, G., Welzl-Mueller, K.: "Audiometrie: Hoerpruefungen im Erwachsenen-und Kindesalter" [Audiometry: Hearing Tests in Adults and Children]. Verlag Hans Huber, Bern, 1988, ISBN: 3-456-81620-0).

In all processes, basically, an acoustic signal is presented which, in a known manner, causes the eardrum to vibrate mechanically, the vibrations are conveyed via the ossicular chain of the middle ear to the inner ear and they are converted there into a neuronal stimulus pattern which leads to a hearing impression.

Especially in objective hearing testing methods (for example, BERA) there are, however, some disadvantages in the type of acoustic excitation, such as for example the magnetic fields generated by the electrodynamic or electromagnetic headphones which are generally used. These magnetic (interference) fields lead to problems in pre-processing and analysis of the evoked potentials which are electrically derived from the skin surface of the head and which can be in the nV range. For acoustic signals monaurally presented supraliminally at medium to high sound levels the problem of "overhearing" of the contralateral ear which is not being tested due to the acoustic sound emission of the headset or by bone conduction continues to occur, which leads to the necessity of acoustic masking of this opposite ear. This effect is undesirable in many psychoacoustic situations, but inevitable.

More recent approaches for partially or fully implantable hearing aids in which (damaged) hearing is no longer acoustically, but mechanically stimulated by direct mechanical coupling of a corresponding transducer to different areas of the middle ear necessitate pre-operative demonstration of the hearing improvement or sound quality to be expected to the subject awaiting implantation. However this is impossible noninvasively with known methods, i.e., without surgery.

SUMMARY OF THE INVENTION

A primary object of the present invention is to circumvent or largely prevent the aforementioned problems by a fundamentally new approach of signal presentation, and to properly enable, in the example of (partially) implantable hearing aids, pre-operative audiological diagnostics.

According to the invention, this object is fundamentally achieved by offering the test or demonstration signals to the hearing, not acoustically, but by direct mechanical stimulation of the ossicular chain of the middle ear, which is accessible from the external auditory canal. For this purpose, a device for electromechanical stimulation and testing of hearing is devised which has an electromechanical transducer for generating mechanical vibrations in the audio range as well as a rigid, mechanical coupling element in order to transmit mechanical vibrations without surgery through the external auditory canal in direct mechanical contact to the center of the eardrum, and thus, to the manubrium of the malleus of the ossicular chain of the middle ear.

In application of the invention, by a suitably trained ENT physician, the vibrating part of the electromechanical transducer is pushed via a suitable coupling element, with optical monitoring and by means of suitable positioning and fixing tools, through the external auditory canal in the central area of the eardrum, the umbo (the site of the eardrum to which the end point of the manubrium is fused), brought mechanically into direct contact with this center, and kept in direct mechanical contact. In this way, the mechanical vibrations of the transducer are coupled directly by mechanical means to the ossicular chain and conveyed to the inner ear, and thus, they lead to an auditory impression.

In particular, to produce audiological test signals, electronic signal generators can be provided with which freely selectable signals can be produced, or signal sources can be used which operate, alternatively or selectively, with audio media, such as magnetic tapes or compact disks. Regardless of the type of signal source, an amplifier with a driving end stage should be provided for supplying the audiologic test signals to the electromechanical transducer.

Insertion of the device according to the invention can be made easier for the examiner, and at the same time for the patient, if the electromechanical transducer is accommodated in a transducer housing which is to be inserted into the entry area of the external auditory canal, with geometrical dimensions which are selected such that the examiner, even when using a microscope, maintains an unobstructed view of the active end of the coupling element which mechanically contacts the center of the eardrum.

Preferably, the coupling element is made as a rod-shaped component which is rigid in the axial direction, with an active end facing away from the transducer which ensures noninjurious mechanical contact to the center of the eardrum. It is especially advantageous if the coupling element is made to be easily manually bent, so that it can be adapted to the individual geometrical shapes of the external auditory canal.

If the coupling element is joined to the transducer, not mechanically fixed, but via a mechanical plug connection, for example, different coupling elements can be implemented which are easily interchangeable for hygienic reasons, and which can be made disposable.

Preferably, the electromechanical transducer, in conjunction with the mechanical coupling element, is made such that the first mechanical resonant frequency is at the top end of the spectral transmission range of ≧10 kHz. In this way, short response times can be achieved due to the broad band.

In order to, furthermore, achieve an impression of the deflection of the active end of the coupling element which is independent of the individual fluctuations of the biological load impedance, the electromechanical transducer is preferably made such that its mechanical source impedance is much greater in the entire spectral transmission range than the mechanical load impedance which is formed by the biological system consisting of the eardrum, ossicular chain, and inner ear.

The examination can be made even less onerous for the patient if the electromechanical transducer is acoustically encapsulated by the design of the transducer housing, such that the acoustic signal which is emitted by the vibrating transducer structures is minimized, and so that, at high stimulation levels, acoustic masking of the contralateral ear not being tested can be abandoned.

In another embodiment of the invention, the system composed of a signal source, amplifier and electromechanical transducer with coupling element is made as a pre-operative diagnosis and demonstration device of the transmission quality to be expected in the application of partially and fully implantable hearing aids.

In order to enable simultaneous binaural stimulation and testing of hearing, the device can be made doubled.

These and further objects, features and advantages of the present invention will become apparent from the following description when taken in connection with the accompanying drawings which, for purposes of illustration only, show a single embodiment in accordance with the present invention.

BRIEF DESCRIPTION OF THE DRAWINGS

The sole FIGURE of the drawings shows a system according to a preferred embodiment of the invention.

DETAILED DESCRIPTION OF THE PREFERRED EMBODIMENT

With reference to the drawing, electrical test signals, for example, pure sinusoidal tones or broadband signals (noise, etc.) are produced by a signal source in the form of a signal generator 10, in which they can be adjusted with respect to functional parameters (frequency, level, time sequences, envelope curves, etc.). These preprocessed signals are amplified with an amplifier 12 which contains a driving end stage which corresponds to the selected transducer principle and they are sent to an electromechanical transducer 14. Alternatively, instead of generating the test signals to be delivered to the amplifier 12 by means of a signal generator 10, the signal source can be signals taken from at least one playback device for producing electrical signals from recorded audio media 16 (e.g., magnetic tapes, compact disks, etc.) as in conventional audiometers.

Transducer 14 can operate according to any known electromechanical conversion principles (dynamic, magnetic, piezoelectric, capacitive/dielectric, magnetostrictive), but, preferably, piezoelectric or capacitive E-field transducer types are selected because of the absence of magnetic interference fields, and transducer 14 is brought near to the inlet of the external auditory canal 18 of the ear being examined using suitable aids. The external dimensions of the transducer 14 are made such that the examiner still has an unobstructed view (broken line of sight 20) through the external auditory canal 18 as far as center 22 (umbo) of eardrum 24. Electromechanical transducer 14 converts the electrical driver signals into mechanical vibrations. These transducer vibrations are transmitted to a coupling element 26 which is mechanically rigid in the direction of its longitudinal axis and which is joined mechanically fixed to the vibrating part of transducer 14 or is connected thereto by means of a plug-in type connection comprising a plug member 38 and a socket member 40. Coupling element 26, which is shown in the drawing as a rod-shaped component, after its end 28 facing away from the transducer 14 having been inserted by the examiner, mechanically contacts the center 22 (umbo) of the eardrum 24 with slight pressure. Thus, the mechanical transducer vibrations are transmitted via the ossicular chain, consisting of the malleus 30, incus 32, and stapes 34, to the inner ear or the cochlea 36 in order to lead to an auditory impression. The end 28 of the rod-shaped coupling element 26 is designed and surface treated, such that, on the one hand, after positioning and insertion, slipping off from umbo 22 is prevented, and on the other hand, the danger of injury to this eardrum area can be excluded.

Since the geometrical dimensions of the external auditory canal 18 are subject to anatomically individual fluctuations and auditory canal 18 runs at a slight angle, rod-shaped coupling element 26 preferably is made such that, on the one hand, it has as high a stiffness as possible in the axial direction to prevent mechanical resonances in the audio range, and on the other hand, it can be easily manually deformed (bent) by the examiner in order to adapt to the slight individual curvature of the auditory canal 18, and thus, to avoid contact of the vibrating coupling element with areas of the external auditory canal. As mentioned above, it is also advantageous if the coupling element 26 is not fixed to transducer 14, but, for example, is connected thereto via plug device 38, 40. In this way, coupling elements of different length can be made for individually different lengths of the external auditory canal 18, and these different coupling elements can be produced inexpensively so as to, thus, be manufactured as disposable articles for hygienic reasons in mass examinations.

More advantageously, the overall electromechanical system formed of the transducer 14 and coupling element 26, with regard to its dynamic parameters mass and stiffness which determine its operating behavior, is dimensioned such that, on the one hand, there is a system set to above resonance, i.e., the first mechanical resonant frequency is at the upper end of the desired transmission frequency range (≧10 kHz). In time behavior, a short transient recovery time of the system is achieved by this broad band; this leads to good pulse transmission behavior of the system. On the other hand, the mechanical source impedance of this system should be clearly above the biological load impedance which is formed by the system eardrum, ossicular chain and coupled hydromechanical inner ear in order to achieve a frequency-independent impression of the deflection of the transducer and thus of the coupling element. In this way, it is possible to compare interindividual audiometry results since the stimulus level is then independent of the unknown, individual variation of the mechanical (biological) load impedances.

The mechanical deflection of coupling element 26 which can be achieved with the overall system consisting of the end stage which drives transducer 14, and transducer 14 itself, for audiologic subjective and objective hearing tests, should achieve values which correspond to an equivalent sound level which is at the upper end of the audiologic dynamic range, therefore, roughly 120 to 130 dB SPL. At low and medium frequencies, this corresponds to roughly 1–2 kHz deflection amplitudes of roughly 1–5 microns.

If the electromechanical transducer is acoustically enclosed within a suitably designed transducer housing 42, the inevitable acoustic sound emission of the vibrating transducer parts at high stimulation levels can be minimized, such that additional acoustic excitation of the tested ear or overhearing by the contralateral ear is eliminated, whereby the necessity of acoustic masking of the contralateral ear is prevented.

If in the case of application of a partially or fully implantable hearing aid, the electromechanical transducer of this implant system is used as the transducer 14, and the signal pre-processing module of this implant system is used as the amplifier 12, the device according to the invention can be used for pre-operative assessment of the transmission quality and suitability of the stipulated implant system for the pertinent proband.

Furthermore, the device according to the invention, in a doubled version, can be used for both ears in a proband for purposes of simultaneous binaural audiometry.

While a single embodiment in accordance with the present invention has been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

I claim:

1. Device for electromechanical stimulation and testing of hearing, comprising an electromechanical transducer for generating mechanical vibrations in an audio range, and a rigid, mechanical coupling element for transmitting the mechanical vibrations, without surgery through an external auditory canal of a patient, in direct mechanical contact to the center of an eardrum for stimulation of the manubrium of the malleus of the ossicular chain of middle ear.

2. Device for electromechanical stimulation and testing according to claim 1, further comprising at least one signal source for generating audiologic test signals, and an amplifier with a driving end stage for delivering audiologic test signals to the electromechanical transducer.

3. Device for electromechanical stimulation and testing according to claim 2, wherein said at least one signal source comprises at least one electronic signal generator.

4. Device for electromechanical stimulation and testing according to claim 2, wherein said at least one signal source comprises at least one playback device for producing electrical signals from recorded audio media.

5. Device for electromechanical stimulation and testing according to claim 4, wherein the recorded audio media is from the group consisting of magnetic tapes and compact disks.

6. Device for electromechanical stimulation and testing according to claim 1, wherein electromechanical transducer is located in a transducer housing which has a size which will permit insertion thereof into an inlet area of the external auditory canal and geometrical dimensions which provide a view of an active end of the coupling element which mechanically contacts the center of the eardrum.

7. Device for electromechanical stimulation and testing according to claim 1, wherein the coupling element is a rod-shaped component which is rigid in an axial direction, and has an active end which faces away from said electromechanical transducer that is shaped for enabling noninjurious mechanical contact with the center of the eardrum.

8. Device for electromechanical stimulation and testing according to claim 7, wherein said coupling element is manually bendable.

9. Device for electromechanical stimulation and testing according to claim 8, wherein mechanical coupling element is joined to the electromechanical transducer by a mechanical plug-type connection.

10. Device for electromechanical stimulation and testing according to claim 1, wherein the system comprised of electromechanical transducer and mechanical coupling element has a first mechanical resonant frequency which is on an upper end of a spectral transmission range of $\geq 10$ kHz.

11. Device for electromechanical stimulation and testing according to claim 1, wherein the electromechanical transducer has a mechanical source impedance which is greater than the mechanical load impedance which is formed by a biological system consisting of the eardrum, ossicular chain and inner ear in the entire spectral transmission range.

12. Device for electromechanical stimulation and testing according to claim 2, wherein the amplifier and the transducer itself are constructed so that the transducer and coupling element when mechanically coupled to an ossicular chain generates maximum deflection amplitudes in the range of 1–5 microns, which correspond to an equivalent sound pressure level of 120–140 dB SPL, in an entire spectral audiologic transmission range.

13. Device for electromechanical stimulation and testing according to claim 1, wherein the electromechanical transducer is acoustically enclosed by a transducer housing as a means for minimizing acoustic signal emissions from vibrating transducer structures at high stimulation levels and thereby eliminating a need for acoustic masking of a contralateral ear not being tested.

14. Device for electromechanical stimulation and testing according to claim 1, wherein the electromechanical transducer is selected from the group consisting of electrodynamic, electromagnetic, magnetostrictive, capacitive, and piezoelectric conversion type electromechanical transducers.

15. Device for electromechanical stimulation and testing according to claim 14, wherein the electromechanical transducer is a piezoelectric conversion type electromechanical transducer.

16. Device for electromechanical stimulation and testing according to claim 1, wherein the device is a preoperative diagnosis and demonstration device; and wherein a signal source, an amplifier and the electromechanical transducer with the mechanical coupling element, as a unit, have a transmission quality corresponding to that of partially and fully implantable hearing aids.

17. Device for electromechanical stimulation and testing according to claim 1, wherein a second electromechanical transducer for generating mechanical vibrations in an audio range, and a second rigid, mechanical coupling element for transmitting the mechanical vibrations are provided for enabling simultaneous binaural stimulation and testing of hearing.

* * * * *